United States Patent
Shinjo et al.

(10) Patent No.: US 11,566,977 B2
(45) Date of Patent: Jan. 31, 2023

(54) MOLECULAR DETECTION APPARATUS

(71) Applicant: Kabushiki Kaisha Toshiba, Minato-ku (JP)

(72) Inventors: Yasushi Shinjo, Kawasaki (JP); Yongfang Li, Kawasaki (JP); Hirohisa Miyamoto, Kamakura (JP); Yutaka Nakai, Yokohama (JP); Reiko Yoshimura, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 715 days.

(21) Appl. No.: 16/561,492

(22) Filed: Sep. 5, 2019

(65) Prior Publication Data

US 2020/0191687 A1 Jun. 18, 2020

(30) Foreign Application Priority Data

Dec. 17, 2018 (JP) .............................. JP2018-235513

(51) Int. Cl.
*H01L 41/04* (2006.01)
*G01N 1/22* (2006.01)
(Continued)

(52) U.S. Cl.
CPC ........... *G01N 1/2273* (2013.01); *G01N 27/02* (2013.01); *G01N 29/036* (2013.01);
(Continued)

(58) Field of Classification Search
CPC .... G01N 1/2273; G01N 27/02; G01N 29/036; G01N 2291/0255; G01N 2291/0256;
(Continued)

(56) References Cited

U.S. PATENT DOCUMENTS

2005/0229677 A1* 10/2005 Tuller ................ B01D 53/9495
73/24.01
2008/0022755 A1 1/2008 Shinbo et al.
(Continued)

FOREIGN PATENT DOCUMENTS

JP  5-281177 A  10/1993
JP  2010-117184 A  5/2010
(Continued)

OTHER PUBLICATIONS

Sapsanis, C, et al., "Insights on Capacitive Interdigitated Electrodes Coated with MOF Thin Films: Humidity and VOCs Sensing as a Case Study", Sensors 2015, 15, 15 pages.
(Continued)

*Primary Examiner* — Richard Tan
(74) *Attorney, Agent, or Firm* — Oblon, McClelland, Maier & Neustadt, L.L.P.

(57) ABSTRACT

A molecular detection apparatus includes a detector. The detector includes: a vibrator having a piezoelectric member that has a first surface and a second surface, a first electrode connected to the first surface, a second electrode connected to the second surface, and a third electrode connected to the second surface and disconnected from the second electrode; a sensitive film overlapping at least one part of the second electrode and at least one part of the third electrode and configured to change a vibration frequency of the vibrator in response to an interaction with target molecules; and a detection electrode to detect the changed vibration frequency.

15 Claims, 10 Drawing Sheets

(51) Int. Cl.
  *G01N 29/036* (2006.01)
  *H01L 41/08* (2006.01)
  *G01N 27/02* (2006.01)
  *H01L 41/047* (2006.01)

(52) U.S. Cl.
  CPC .......... *H01L 41/042* (2013.01); *H01L 41/047* (2013.01); *H01L 41/0825* (2013.01)

(58) Field of Classification Search
  CPC .. G01N 29/022; G01N 33/0047; G01N 33/22; G01N 1/2214; H01L 41/042; H01L 41/047; H01L 41/0825; H01L 41/1136; H01L 41/094
  USPC .......................................................... 422/98
  See application file for complete search history.

(56) References Cited

U.S. PATENT DOCUMENTS

| | | | |
|---|---|---|---|
| 2017/0173623 A1 | 6/2017 | Britt et al. | |
| 2017/0248565 A1 | 8/2017 | Yamada et al. | |
| 2018/0003604 A1* | 1/2018 | Shiba | G01N 21/49 |
| 2018/0202961 A1* | 7/2018 | Sussner | G01N 29/022 |

FOREIGN PATENT DOCUMENTS

| | | |
|---|---|---|
| JP | 2011-203008 A | 10/2011 |
| JP | 2012-220454 A | 11/2012 |
| JP | WO2016/121155 A1 | 8/2016 |
| JP | 2017-156346 A | 9/2017 |
| WO | WO 2006/006587 A1 | 1/2006 |
| WO | WO 2018/136556 A1 | 7/2018 |

OTHER PUBLICATIONS

Stavila, V, et al., "Kinetics and mechanism of metal-organic framework thin film growth: Systematic investigation of HKUST-1 deposition on QCM electrodes", The Royal Society of Chemistry, 2012, 2, 7 pages.

Lv, Y, et al., "Ni—MOF-74 as sensing material for resonant-gravimetric detection of ppb-level CO", Sensors and Actuators B: Chemical 262 (2018), pp. 562-569.

Bloch, E, et al., "Metal Insertion on a Microporous Metal-Organic Framework Lined with 2, 2'-Bipyridine", J. Am. Chem. Soc. 2010, 132, pp. 14382-14384.

Yamagiwa, H, et al., "Detection of Volatile Organic Compounds by Weight-Detectable Sensors coated with Metal-Organic Frameworks", Scientific Reports, vol. 4, Article No. 6247, 2014, 6 pages.

* cited by examiner

MOLECULAR DETECTION APPARATUS

CROSS-REFERENCE TO RELATED APPLICATIONS

This application is based upon and claims the benefit of priority from Japanese Patent Application No. 2018-235513, filed on Dec. 17, 2018; the entire contents of which are incorporated herein by reference.

FIELD

Embodiments of the present invention relate to a molecular detection apparatus.

BACKGROUND

A sensing technology using a smell (gas) sensor has been widely used for odor determination, measurement of volatile organic compounds (VOC) in the atmosphere, performance confirmation of air cleaners, trouble detection of devices, and so on because it is capable of digitizing smell in the air.

In recent years, there have been increasing concerns of detection of detonating explosives and detection of narcotic drugs and stimulant drugs and a concern of exhalation diagnosis of specific diseases, which have relied on the dog's sense of smell so far, and higher performance of a smell sensor and a gas sensor has been desired.

General gas sensing methods use devices such as a flame ionization detector (FID), a photo-ionization detector (PID), and a non-dispersive infra-red (NDIR) gas analyzer. These devices have problems regarding portability, risk due to the use of a flammable gas, life and price of a light source used for the measurement, substance recognition performance, and so on. Therefore, a small sensor advantageous in the assembly in a processing device and the measurement at a work site has been developed.

The performances required in the smell (gas) sensor are sensitivity, selectivity, simplicity, swiftness, reliability, stability, and so on. As a semiconductor gas sensor that is a representative of a small sensor, there has been proposed a sensor that is capable of measuring gas concentration by using a change that electrical properties such as electrical resistance undergo when oxygen adsorbed on porous tin oxide ($SnO_2$) is consumed by a reducing substance. However, a conventionally used oxide semiconductor sensor has a problem of low detection sensitivity and detection accuracy, for example. The detection accuracy means accuracy in detecting a type, accuracy in detecting a concentration of a detected gas, for example, and so on.

DETAILED DESCRIPTION

A molecular detection apparatus in an embodiment comprises a detector. The detector includes: a vibrator having a piezoelectric member that has a first surface and a second surface, a first electrode connected to the first surface, a second electrode connected to the second surface, and a third electrode connected to the second surface and disconnected from the second electrode; a sensitive film overlapping at least one part of the second electrode and at least one part of the third electrode and configured to change a vibration frequency of the vibrator in response to an interaction with target molecules; and a detection electrode to detect the changed vibration frequency.

Embodiments will be hereinafter explained with reference to the drawings. In the embodiments, substantially the same constituent parts are denoted by the same reference sign, and explanation thereof may be partly skipped. The drawings are schematic, and the relation between the thickness and planar dimension of each part, and a thickness ratio among parts, and so on may be different from actual ones.

First Embodiment

Figure 1:
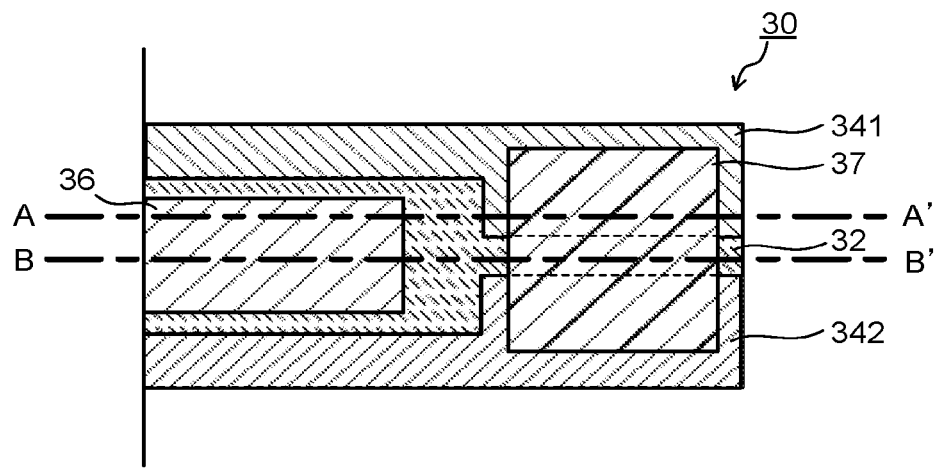
FIG. 1 is a top view illustrating a structure example of a detector.
Figure 2:
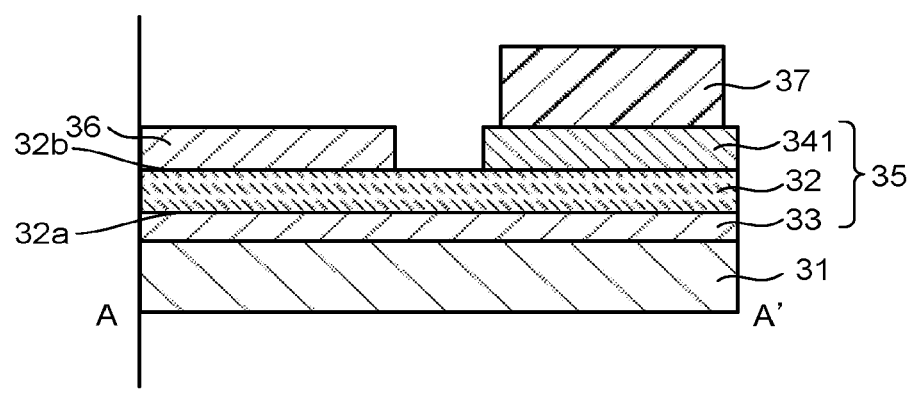
FIG. 2 is a cross-sectional view taken along a line segment A-A' in FIG. 1.
Figure 3:
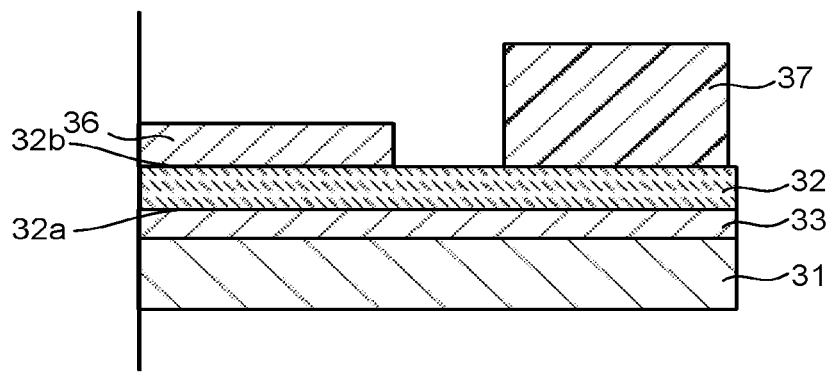
FIG. 3 is a cross-sectional view taken along a line segment B-B' in FIG. 1.

There will be explained a configuration example of a detector used in a molecular detection apparatus in the embodiment. FIG. 1 is a top view illustrating a structure example of a detector 30, FIG. 2 is a cross-sectional view taken along a line segment A-A' in FIG. 1, and FIG. 3 is a cross-sectional view taken along a line segment B-B' in FIG. 1.

The detector 30 includes a vibrator 35 including a piezoelectric member 32, an electrode 33, an electrode 341, and an electrode 342, an electrode 36, and a sensitive film 37. The piezoelectric member 32, the electrode 33, the electrode 341, the electrode 342, the electrode 36, and the sensitive film 37 are stacked on a base 31, for example. The detector 30 may have a beam shape with, for example, at least one portion thereof being fixed.

The base 31 is formed by using, for example, silicon, glass, resin, and so on. The base 31 has a function as a support to support the detector 30.

The piezoelectric member 32 has a surface 32a and a surface 32b on the side opposite to the surface 32a. The piezoelectric member 32 is deformed by a predetermined voltage being applied thereto. Thus, the piezoelectric member 32 expands and contracts by, for example, an alternating voltage being applied thereto, thereby making it possible to vibrate the detector 30. The piezoelectric member 32 is formed by using, for example, lead zirconate titanate (PZT), a solid solution of lead zinc niobate-lead titanate (PZN-PT), a solid solution of lead manganate niobate-lead zirconate titanate (PMnN-PZT), aluminum nitride (AlN), zinc oxide (ZnO), potassium sodium niobate (KNN), lithium niobate ($LiNnO_3$), and so on.

The electrode 33 is electrically connected to the surface 32a, for example. The electrode 33 is provided in contact with the surface 32a, for example. The electrode 33 has a function as a driving electrode for driving the piezoelectric member 32 to vibrate the vibrator 35. The electrode 33 is formed by using metal materials such as Pt, Au, Mo, W, and Al, for example.

The electrode 341 is electrically connected to the surface 32b. The electrode 341 is provided in contact with the surface 32b, for example. The electrode 341 has a function as a driving electrode for driving the piezoelectric member 32 to vibrate the vibrator 35. The electrode 341 may have a function as a functional electrode for measuring an impedance of the sensitive film 37. Further, the electrode 341 may have a function as a heater for heating the sensitive film 37.

The electrode 341 is electrically connected to the surface 32b. The electrode 342 is provided in contact with the surface 32b, for example, and is apart from the electrode 341. The electrode 342 is electrically disconnected from the electrode 341, for example. The electrode 342 has a function as a driving electrode for driving the piezoelectric member 32 to vibrate the vibrator 35. The electrode 342 may have a function as a functional electrode for measuring an impedance of the sensitive film 37. The electrode 342 may have a function as a heater for heating the sensitive film 37 to desorb molecules attached to or adsorbed on the sensitive film 37.

The electrode 36 has a function as a detection electrode to detect a changed vibration frequency. Vibration frequency is, for example, resonant frequency. The electrode 36 is electrically connected to the surface 32a or the surface 32b. The electrode 36 is provided in contact with the surface 32b, for example, and is apart from the electrode 341 and the electrode 342. The electrode 36 is electrically disconnected from the electrode 341 and the electrode 342. This embodiment is not limited to this, and the electrode 36 may be provided in contact with the surface 32a and may be apart from the electrode 33. At this time, the electrode 36 is electrically disconnected from the electrode 33.

The electrode 341, the electrode 342, and the electrode 36 are formed by using metal materials such as Pt, Au, Mo, W, and Al, for example. Incidentally, the electrode 341, the electrode 342, and the electrode 36 may be formed simultaneously by patterning the same conductive film.

The sensitive film 37 overlaps the electrode 341 and the electrode 342. The sensitive film 37 may be provided in contact with at least one portion of a side surface of the electrode 341, at least one portion of a side surface of the electrode 342, and a region between the electrode 341 and the electrode 342 on the surface 32b.

The sensitive film 37 changes the vibration frequency of the vibrator 35 by an interaction with target molecules. The sensitive film 37 changes the vibration frequency of the vibrator 35 by attachment or adsorption of, for example, target molecules having mass to or on the sensitive film 37. The sensitive film 37 has an exposed surface and the exposed surface is not in contact with the electrode 341 and the electrode 342. This makes it possible to increase the volume of a region capable of interacting with target molecule as compared to the case where the electrode 341 and the electrode 342 are formed on the sensitive film 37.

The sensitive film 37 is formed by using materials that easily attach or adsorb specific molecules selectively, which are, for example, polymers or bio-membranes, inorganic fine particles (metal oxides or the like), metal nanoparticles, activated carbons, zeolites, organometallic complexes, metal organic frameworks (MOFs), and so on.

MOFs are microporous materials consisting of metal ions or clusters coordinated to organic ligands that have large surface areas exceeding activate carbons and zeolites. They are expected to be applied to gas adsorption, a separation technique, a sensor, a catalyst, and so on. MOFs are capable of uptaking target molecules and concentrating them even when the number of target molecules is very small. Therefore, using the MOFs for the sensitive film 37 makes it possible to improve the detection sensitivity of target molecules. Further, MOFs are easily capable of customizing the type and the size of metal species and the organic ligands, so that selectivity of target molecules can be imparted, leading to an improvement in the detection accuracy of target molecules.

In the case where the target molecules are gas molecules at normal temperature and pressure, the MOF preferably has coordinatively unsaturated metal sites. The coordinative unsaturation means a state where a metal ion has at least one vacant site in its coordination state, and the gas molecules strongly interact with such a site. Examples of MOFs having such coordinatively unsaturated metal sites as a metal nodes include HKUST-1, MIL-100 (Cr, Fe), MIL-101 (Cr, Fe), UIO-66, UIO-67, CPO-27 (Co, Fe, Mg, Ni), and so on.

In the case where the organic ligand itself has a coordinatively unsaturated metal sites separately from the metal node being the framework of the MOF, the metal node does not necessarily need to be coordinatively unsaturated. For example, MOFs using crosslinkable coordination compounds are cited. Examples of such organic ligands include bipyridine derivatives. For example, Al(OH)(bpydc)(MOF-253) that is obtained from 2,2'-bipyridine-5,5'-dicarboxylic acid ($h_2bpydc$) and $AlCl_3.6H_2O$ becomes a MOF having unsaturated active metal sites by coordination of Pd or Cu to bipyridine through a reaction with $PdCl_2$ or $CuBF_4$.

Figure 4:
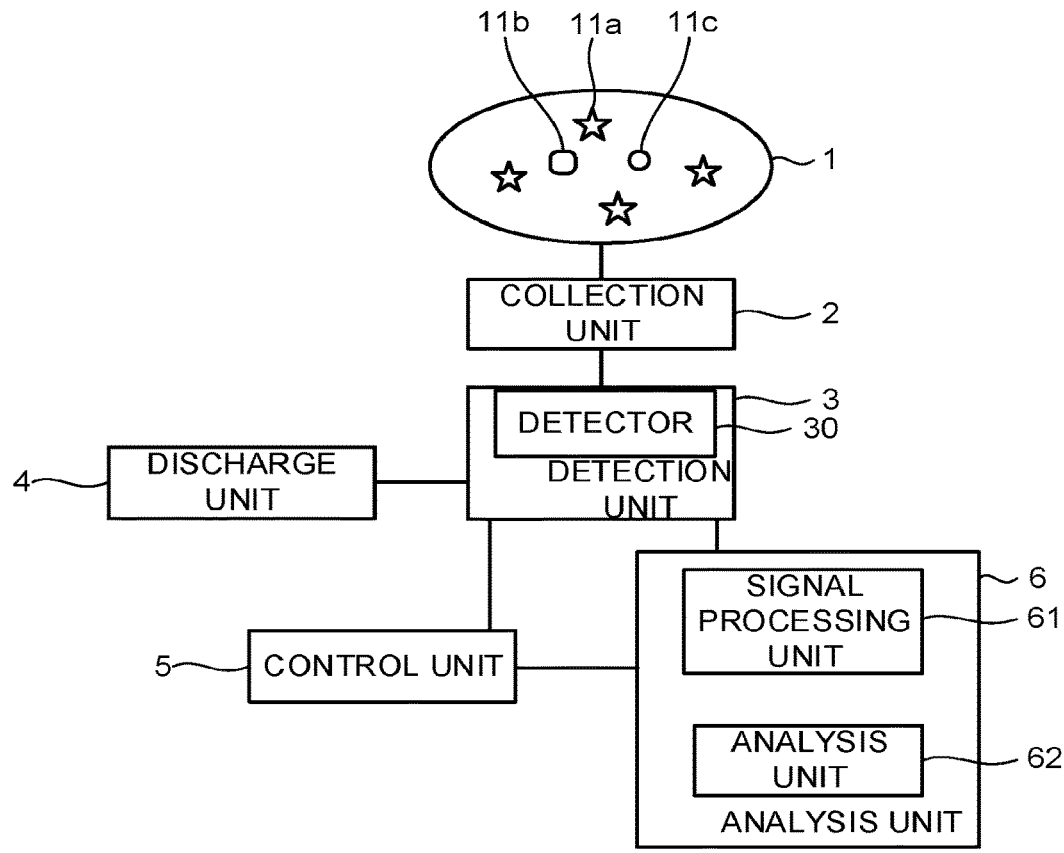
FIG. 4 is a block diagram illustrating a configuration example of a molecular detection apparatus.

Next, there will be explained a configuration example of the molecular detection apparatus. FIG. 4 is a block diagram illustrating the configuration example of the molecular detection apparatus in the embodiment. The molecular detection apparatus illustrated in FIG. 4 includes a collection unit 2, a detection unit 3, a discharge unit 4, a control unit 5, and an analysis unit 6.

The collection unit 2 collects a fluid 1 containing target molecules 11a. The fluid 1 is liquid or gas. The collection unit 2 has a collection port for the fluid 1 and is connected to a pump through a flow path. The collection unit 2 drives the pump to thereby collect the fluid 1 through the collection port to send it to the detection unit 3. The collection unit 2 may include a filter that removes impurities such as fine particles contained in the fluid 1. Incidentally, a valve may be provided in place of the pump and start and stop of the introduction of the fluid 1 may be controlled by opening/closing the valve.

The fluid 1 sometimes contains, as impurities, substances having a molecular weight and a molecular structure similar to the molecular weight and the molecular structure of the target molecules 11a, and so on. Further, the target molecules 11 floating in the air are often present in a state of a mixture with various contaminants 11b such as smell components and fine particles and moisture 11c. Because of this, the fluid 1 may be pre-processed by a filter device and so on in advance to be thereafter sent to the molecular detection apparatus. Examples of the target molecules 11a include moisture, volatile organic compounds (benzene, toluene, xylene, hexane, pentane, methanol, ethanol, acetone, ethyl acetate, chloroform, dichloromethane, flons, formaldehyde, furfural, and so on), and geosmin and 2-methylisoborneol that cause a mold odor, in addition to rare gases such as xenon and krypton, gaseous substances at normal temperature and pressure such as hydrogen, oxygen, nitrogen, nitrogen oxide, hydrogen sulfide, ammonia, carbon monoxide, carbon dioxide, methane, ethane, propane, ethylene, and acetylene, gunpowder and explosives such as 2,4,6-trinitrotoluene and dinitrotoluene, and illicit drugs such as methamphetamine and amphetamine.

The fluid 1 collected in the collection unit 2 is sent to the detection unit 3 in the flow path. The detection unit 3 is arranged in the flow path. The detection unit 3 includes the detector 30. Incidentally, the detection unit 3 may include a plurality of the detectors 30. The plural detectors 30 preferably include sensitive films 37 different from one another. This makes it possible to increase types of data to be detected, so that it is possible to improve the detection accuracy of the target molecules 1a.

The discharge unit 4 has a function to discharge the fluid 1 from the detection unit 3. The discharge unit 4 has a discharge port for the fluid 1 and is connected to the pump through the flow path. The discharge unit 4 drives the pump to thereby suck the fluid 1 in the detection unit 3 and discharge the fluid 1 through the discharge port.

Figure 5:
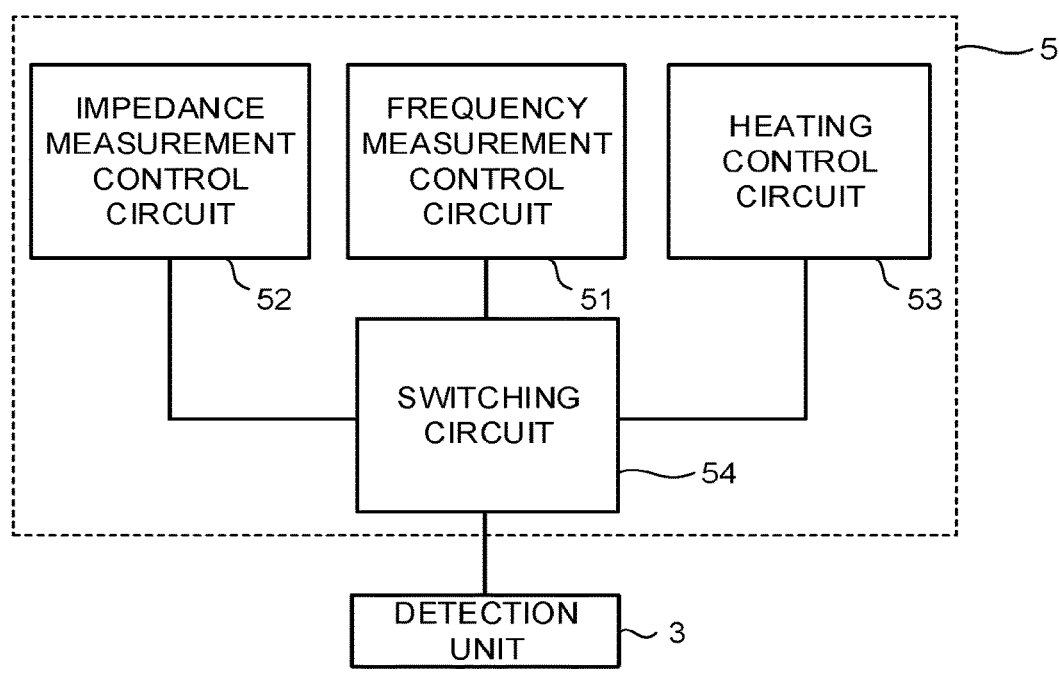
FIG. 5 is a block diagram illustrating a configuration example of a control unit.

The control unit 5 is electrically connected to the electrode 33, the electrode 341, the electrode 342, and the electrode 36, for example. FIG. 5 is a block diagram illustrating a configuration example of the control unit 5. The control unit 5 illustrated in FIG. 5 includes a frequency measurement control circuit 51 that controls measurement of the vibration frequency of the vibrator 35, an impedance measurement control circuit 52 that controls measurement of the impedance of the sensitive film 37, a heating control circuit 53 that controls heating of the sensitive film 37, and a switching circuit 54 that switches among connection between the detector 30 and the frequency measurement control circuit 51, connection between the detector 30 and the impedance measurement control circuit 52, and connection between the detector 30 and the heating control circuit 53. The frequency measurement control circuit 51, the impedance measurement control circuit 52, the heating control circuit 53, and the switching circuit 54 are each controlled by control signals from a processor and so on, for example.

The frequency measurement control circuit 51 controls application of a first voltage between the electrode 33 and the electrode 341 and the electrode 342. The frequency measurement control circuit 51 applies the first voltage between the electrode 33 and the electrode 341 and the electrode 342, for example, to thereby vibrate the vibrator 35. The first voltage is an alternating voltage, for example. The frequency measurement control circuit 51 has a power supply for applying the first voltage and a measuring device to measure the vibration frequency.

The impedance measurement control circuit 52 controls application of a second voltage between the electrode 341 and the electrode 342. The impedance measurement control circuit 52 applies the second voltage between the electrode 341 and the electrode 342, for example, to measure the impedance of the sensitive film 37. The second voltage is a direct-current voltage or an alternating voltage, for example. The impedance measurement control circuit 52 has a power supply for applying the second voltage and a measuring device to measure the impedance.

The heating control circuit 53 controls application of a third voltage to the electrode 341 and the electrode 342. The heating control circuit 53 applies the third voltage to the electrode 341 and the electrode 342, for example, to thereby heat the sensitive film 37 and desorb the target molecules 11a attached to or adsorbed on the sensitive film 37. The third voltage is a direct-current voltage or an alternating voltage, for example. The heating control circuit 53 has a power supply for applying the third voltage, for example. A heating temperature is adjusted by controlling the value of the third voltage, for example.

The switching circuit 54 switches among connection between the electrode 33, the electrode 341, the electrode 342, and the electrode 36 and the frequency measurement control circuit 51, connection between the electrode 33, the electrode 341, the electrode 342, and the electrode 36 and the impedance measurement control circuit 52, and connection between the electrode 33, the electrode 341, the electrode 342, and the electrode 36 and the heating control circuit 53. The switching circuit 54 has a plurality of switches, for example.

The analysis unit 6 detects at least one selected from the group consisting of a type and a concentration of the target molecules 11a in accordance with at least one piece of data selected from the group consisting of data indicating the change in the vibration frequency of the vibrator 35 caused by attachment or adsorption of molecules to or on the sensitive film 37, data indicating the change in the impedance of the sensitive film 37, and data indicating the change in the above-described vibration frequency caused by desorption of molecules from the sensitive film 37. In the case of including a plurality of the detectors 30, the analysis unit 6 detects at least one selected from the group consisting of the type and the concentration of the target molecules 11a in accordance with at least one piece of data selected from the group consisting of data indicating the change in the vibration frequency of the vibrator 35 caused by attachment or adsorption of molecules to or on the sensitive film 37, data indicating the change in the impedance of the sensitive film 37, and data indicating the change in the above-described vibration frequency caused by desorption of molecules from the sensitive film 37 in each of the plural detectors 30. The analysis unit 6 includes a signal processing unit 61 that processes measured data and an analyzer 62 that analyzes at least one of the type and the concentration of the target molecules 11a in accordance with the processed data.

As above, in the molecular detection apparatus in this embodiment, the electrodes 341, 342 are provided as a driving electrode for the vibrator 35, thereby making it possible to impart the function of measuring the impedance of the sensitive film 37 and the function as a heater for desorbing molecules attached to or adsorbed on the sensitive film 37 to the driving electrodes. This makes it possible to measure the change in the vibration frequency of the vibrator responsive to the adsorption or desorption of molecules on or from the sensitive film 37, the polarity of the molecules, a dielectric constant, and the change in the impedance corresponding to humidity in the atmosphere, and accelerate the desorption of the molecules attached to or adsorbed on the sensitive film 37 by heating in the detector 30. Further, providing the electrode 341 and the electrode 342 increases a contact area between the driving electrodes and the sensitive film 37, thereby making it possible to facilitate generation of an interaction between the sensitive film 37 and the target molecules. Furthermore, the electrode 341 and the electrode 342 can be formed on the same surface, and thus can be formed in the same process, resulting in that it is possible to suppress an increase in the number of processes.

Second Embodiment

Figure 6:
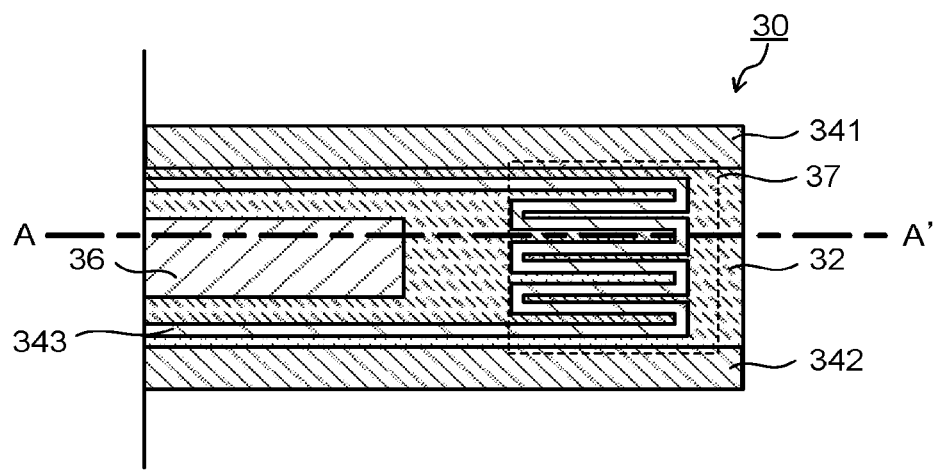
FIG. 6 is a top view illustrating another structure example of the detector.
Figure 7:
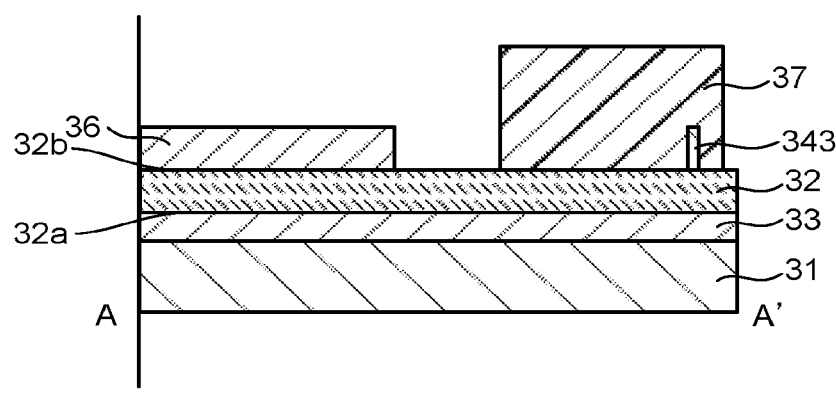
FIG. 7 is a cross-sectional view taken along a line segment A-A' in FIG. 6.

The structure of the detector 30 is not limited to the structure illustrated in FIG. 1 to FIG. 3. FIG. 6 is a top view illustrating another structure example of the detector 30 and FIG. 7 is a cross-sectional view taken along a line segment A-A' in FIG. 6. Incidentally, it is possible to appropriately cite the explanations in FIG. 1 to FIG. 3 regarding the parts common to those in FIG. 1 to FIG. 3.

The detector 30 illustrated in FIG. 6 and FIG. 7 is different from the detector 30 illustrated in FIG. 1 to FIG. 3 in further including an electrode 343. Incidentally, the sensitive film 37 is illustrated by a dotted line in FIG. 6 for convenience.

The electrode 343 is electrically connected to the surface 32b and is electrically disconnected from the electrode 341 and the electrode 342. The electrode 343 is provided in contact with the surface 32b, for example, and is apart from the electrode 341 and the electrode 342. The electrode 343 is electrically connected to the switching circuit 54 and is electrically disconnected from the electrode 341 and the electrode 342. The electrode 343 has a function as a heater that heats, for example, the sensitive film 37 to desorb the molecules attached to or adsorbed on the sensitive film.

The electrode 343 has a serpentine shape that continuously bends between the surface 32b and the sensitive film 37, for example. Increasing a contact area between the electrode 343 and the sensitive film 37 makes it possible to facilitate heating of the sensitive film 37. The electrode 343 is formed by using materials applicable to the electrode 341 and the electrode 342, for example. Incidentally, the electrode 341, the electrode 342, and the electrode 343 may be formed simultaneously by patterning the same conductive film.

Third Embodiment

Figure 8:
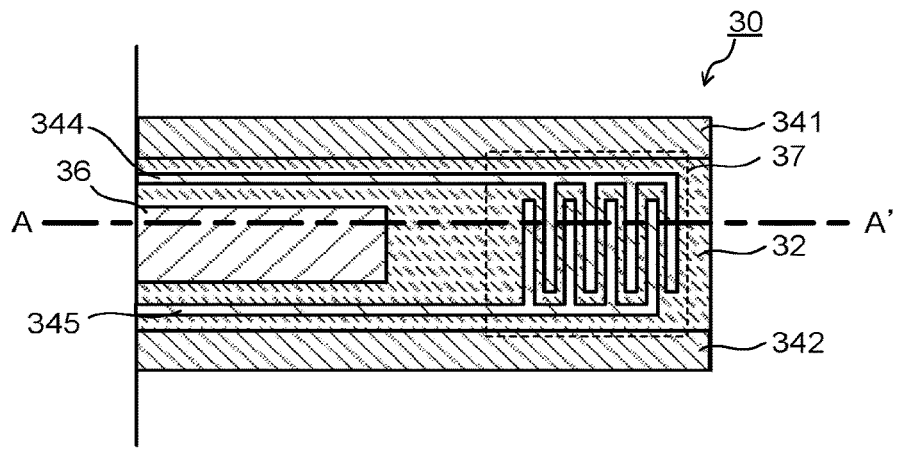
FIG. 8 is a top view illustrating another structure example of the detector.
Figure 9:
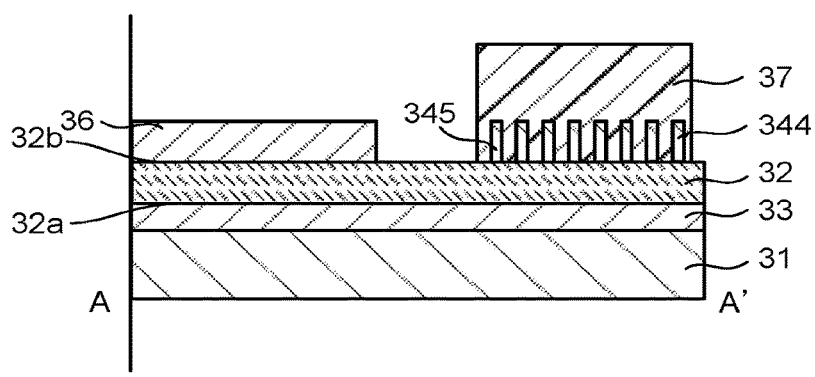
FIG. 9 is a cross-sectional view taken along a line segment A-A' in FIG. 8.

FIG. 8 is a top view illustrating another structure example of the detector 30, and FIG. 9 is a cross-sectional view taken along a line segment A-A' in FIG. 8. Incidentally, it is possible to appropriately cite the explanations in FIG. 1 to FIG. 3 regarding the parts common to those in FIG. 1 to FIG. 3.

The detector 30 illustrated in FIG. 8 and FIG. 9 is different from the detector 30 illustrated in FIG. 1 to FIG. 3 in further including an electrode 344 and an electrode 345. Incidentally, the sensitive film 37 is illustrated by a dotted line in FIG. 8 for convenience.

The electrode 344 is electrically connected to the surface 32b and is electrically disconnected from the electrode 341 and the electrode 342. The electrode 344 is provided in contact with the surface 32b, for example, and is apart from the electrode 341 and the electrode 342. The electrode 344 is electrically connected to the switching circuit 54 and is electrically disconnected from the electrode 341 and the electrode 342. The electrode 343 may have a function as a functional electrode for measuring the impedance of the sensitive film 37 and a function as a heater that heats the sensitive film 37 to desorb the molecules attached to or adsorbed on the sensitive film.

The electrode 345 is electrically connected to the surface 32b and is electrically disconnected from the electrode 341 to the electrode 344. The electrode 345 is provided in contact with the surface 32b, for example, and is apart from the electrode 341 to the electrode 344. Therefore, the electrode 345 is electrically connected to the switching circuit 54 and is electrically disconnected from the electrode 341 to the electrode 344. The electrode 345 may have a function as a functional electrode for measuring the impedance of the sensitive film 37 and a function as a heater that heats the sensitive film 37 to desorb the molecules attached to or adsorbed on the sensitive film.

The electrode 344 and the electrode 345 each have a comb-teeth shape, the comb-teeth shapes facing each other, between the surface 32b and the sensitive film 37, for example. Increasing a contact area between the electrode 344 and the electrode 345 and the sensitive film 37 makes it possible to facilitate measurement of the impedance of the sensitive film 37 and facilitate heating of the sensitive film 37, for example. The electrodes 344, 345 are formed by using materials applicable to the electrodes 341, 342, for example.

Figure 10:
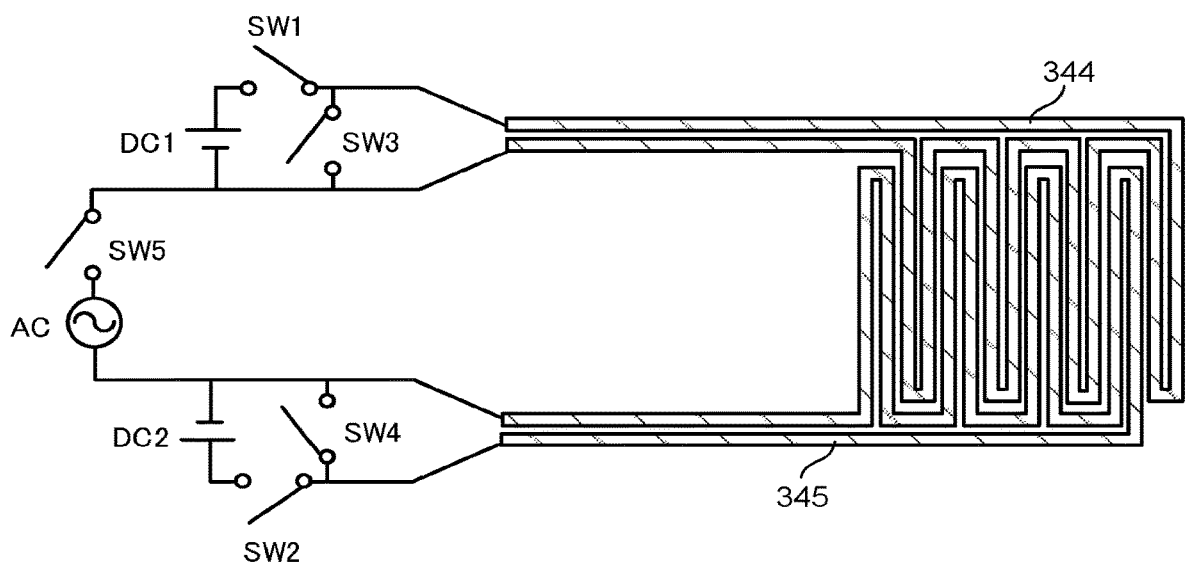
FIG. 10 is a view illustrating a structure example of an electrode 344 and an electrode 345.

FIG. 10 is a view illustrating a structure example of the electrode 344 and the electrode 345. The electrode 344 and the electrode 345 illustrated in FIG. 10 each form a serpentine shape by bending continuously and a comb-teeth shape, the comb-teeth shapes facing each other, between the surface 32b and the sensitive film 37, for example. Increasing a contact area between the electrode 344 and the electrode 345 and the sensitive film 37 makes it possible to facilitate measurement of the impedance of the sensitive film 37 and facilitate heating of the sensitive film 37, for example.

A switch SW1 and a switch SW2 in the switching circuit 54, for example, are brought into an on state, and thereby the electrode 344 and the electrode 345 are connected to a direct-current power supply DC1 and a direct-current power supply DC2 in the heating control circuit 53 and receive supply of a direct-current voltage to then be heated. Further, a switch SW3, a switch SW4, and a switch SW5 in the switching circuit 54, for example, are brought into an on state, and thereby the electrode 344 and the electrode 345 are connected to an alternating-current power supply AC in the impedance measurement control circuit 52 to receive supply of an alternating voltage, thereby being capable of measuring the impedance of the sensitive film 37.

Fourth Embodiment

Figure 11:
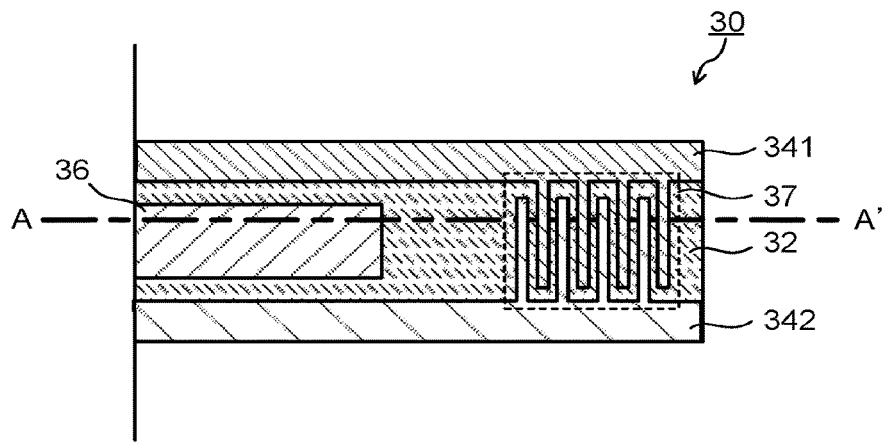
FIG. 11 is a top view illustrating another structure example of the detector.
Figure 12:
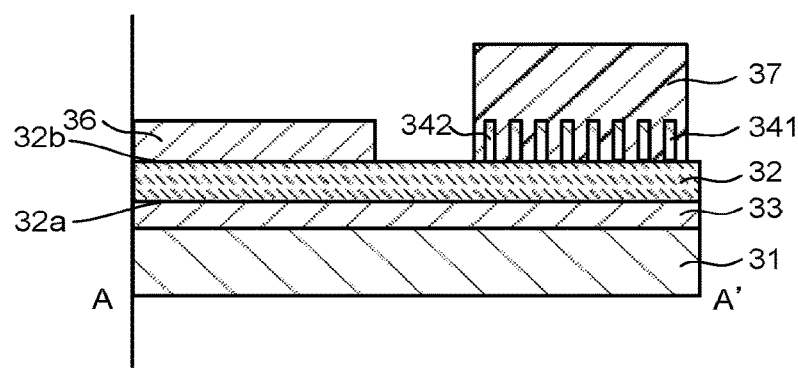
FIG. 12 is a cross-sectional view taken along a line segment A-A' in FIG. 11.

FIG. 11 is a top view illustrating another structure example of the detector 30, and FIG. 12 is a cross-sectional view taken along a line segment A-A' in FIG. 11. Incidentally, it is possible to appropriately cite the explanations in FIG. 1 to FIG. 3 regarding the parts common to those in FIG. 1 to FIG. 3.

The detector 30 illustrated in FIG. 11 and FIG. 12 is different from the detector 30 illustrated in FIG. 1 to FIG. 3 in that the electrode 341 and the electrode 342 each have a comb-teeth shape, the comb-teeth shapes facing each other, between the surface 32b and the sensitive film 37. Incidentally, the sensitive film 37 is illustrated by a dotted line in FIG. 11 for convenience.

Increasing a contact area between the electrode 341 and the electrode 342 and the sensitive film 37 makes it possible to facilitate measurement of the impedance of the sensitive film 37 and facilitate heating of the sensitive film 37, for example.

Figure 13:
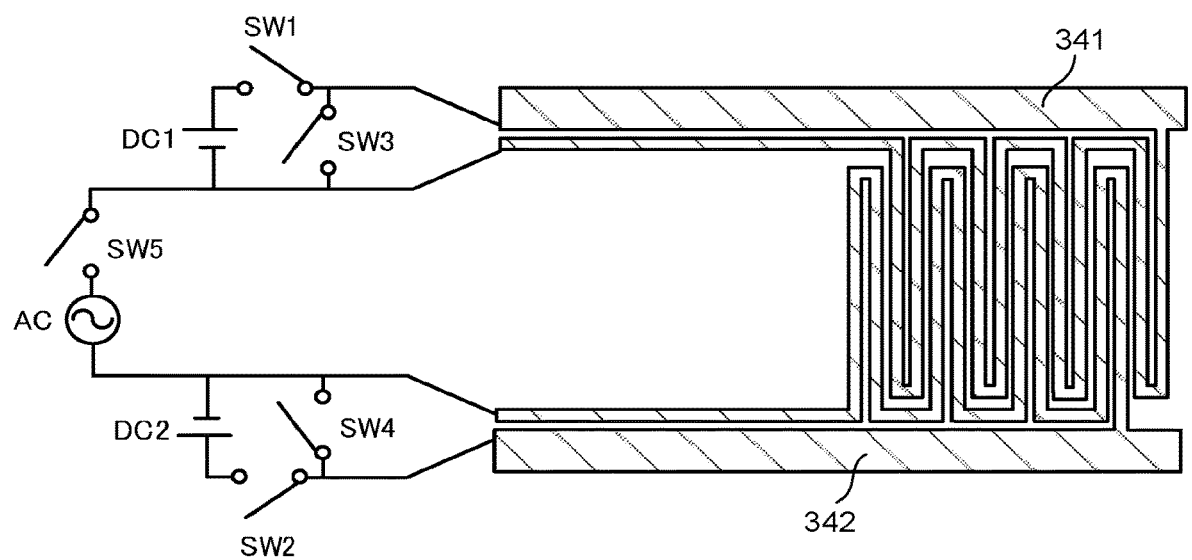
FIG. 13 is a view illustrating a structure example of an electrode 341 and an electrode 342.

FIG. 13 is a view illustrating a structure example of the electrode 341 and the electrode 342. The electrode 341 and the electrode 342 illustrated in FIG. 13 each form a serpentine shape by bending continuously and a comb-teeth shape, the comb-teeth shapes facing each other, between the surface 32b and the sensitive film 37, for example. Increasing a contact area between the electrode 341 and the electrode 342 and the sensitive film 37 makes it possible to facilitate measurement of the impedance of the sensitive film 37 and facilitate heating of the sensitive film 37, for example.

The switch SW1 and the switch SW2 in the switching circuit 54, for example, are brought into an on state, and thereby the electrode 341 and the electrode 342 are connected to the direct-current power supply DC1 and the direct-current power supply DC2 in the heating control circuit 53 respectively and receive supply of a direct-current voltage to then be heated. Further, the switch SW3, the switch SW4, and the switch SW5 in the switching circuit 54, for example, are brought into an on state, and thereby the electrode 341 and the electrode 342 are connected to the alternating-current power supply AC in the impedance measurement control circuit 52 to receive supply of an alternating voltage, thereby being capable of measuring the impedance of the sensitive film 37.

Figure 14:
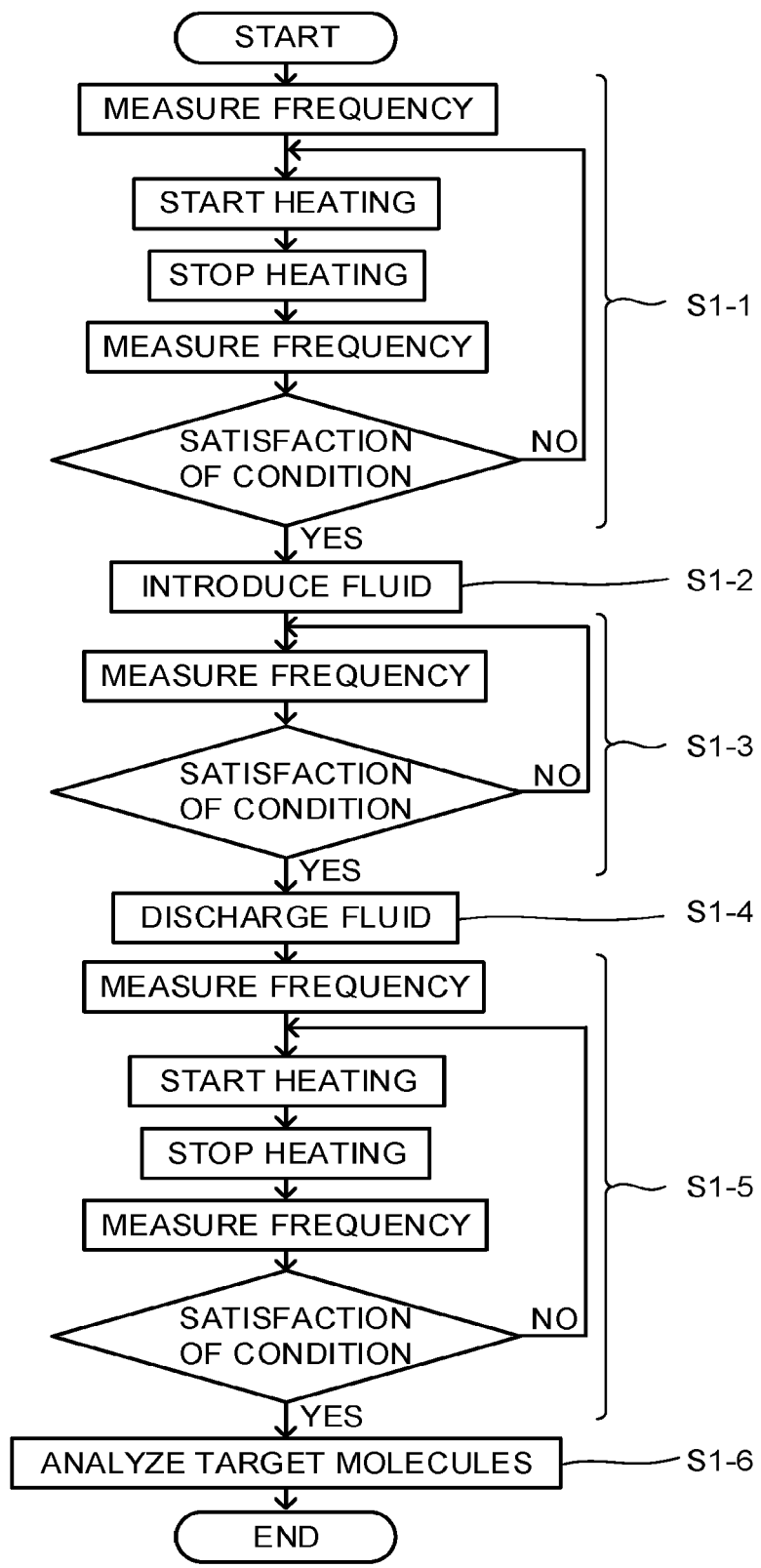
FIG. 14 is a flowchart for explaining an example of a detection method of target molecules.

Then, there will be explained a detection method example of the target molecules 11a using the molecular detection apparatus in the embodiment. FIG. 14 is a flowchart for explaining the detection method example.

The detection method example includes, as illustrated in FIG. 14, a sensitive film initialization and initial value acquisition step S1-1, a fluid introduction step S1-2, a measurement step of frequency change caused by adsorption S1-3, a fluid discharge step S1-4, a measurement step of frequency change caused by desorption S1-5, and a target molecule analysis step S1-6. This example is applicable to the case where the detector 30 has the structure illustrated in FIG. 1 to FIG. 3 or the structure illustrated in FIG. 11 to FIG. 13, for example, and the driving electrodes for driving the vibrator 35 function as a heater.

At the sensitive film initialization and initial value acquisition step S1-1, first, the switching circuit 54 connects the detector 30 and the frequency measurement control circuit 51 and the first voltage is applied between the electrode 33 and the electrode 341 and the electrode 342, to thereby vibrate the vibrator 35 and measure an initial vibration frequency of the vibrator 35. Then, the switching circuit 54 cancels the connection between the detector 30 and the frequency measurement control circuit 51, and connects the detector 30 and the heating control circuit 53 and the third voltage is applied to the electrode 341 and the electrode 342, to thereby heat the sensitive film 37 and desorb the molecules attached to or adsorbed on the sensitive film 37. At this time, a temperature sensor (not illustrated) may be provided separately to control the temperature to a predetermined temperature. After a lapse of a predetermined time period, the switching circuit 54 cancels the connection between the detector 30 and the heating control circuit 53 to stop the heating. Then, the switching circuit 54 connects the detector 30 and the frequency measurement control circuit 51 and the first voltage is applied between the electrode 33 and the electrode 341 and the electrode 342, to thereby vibrate the vibrator 35, measure the vibration frequency of the vibrator 35, and acquire a difference between an initial value and a saturation value of the vibration frequency, for example, as data indicating the change in the vibration frequency. Incidentally, the ratio of a saturation value to an initial value of the vibration frequency may be acquired as the data indicating the change in the vibration frequency. The measurement is finished at the point when the vibration frequency satisfies a predetermined determination condition, for example, a condition such that a change value or change rate of the frequency per unit time becomes a threshold value or less and initialization is completed.

At the fluid introduction step S1-2, the fluid 1 is introduced into the detection unit 3 from the collection unit 2. The target molecules 11a contained in the fluid 1 are attached to or adsorbed on the sensitive film 37 in the detector 30.

At the measurement step of frequency change caused by adsorption S1-3, the switching circuit 54 connects the detector 30 and the frequency measurement control circuit 51 and the first voltage is applied between the electrode 33 and the electrode 341 and the electrode 342, to thereby vibrate the vibrator 35 and measure the vibration frequency of the vibrator 35.

At the measurement step of frequency change caused by adsorption S1-3, the difference between an initial value and a saturation value of the vibration frequency, for example, is acquired as data indicating the change in the vibration frequency. Incidentally, the ratio of a saturation value to an initial value of the vibration frequency may be acquired as the data indicating the change in the vibration frequency. Measuring the vibration frequency is continued until the vibration frequency satisfies a predetermined determination condition, for example, a condition such that a change amount or change rate of the vibration frequency per unit time becomes a threshold value or less. This makes it possible to confirm the desorption of a substance adsorbed on or attached to the sensitive film 37.

At the fluid discharge step S1-4, the fluid 1 is discharged through the discharge unit 4.

At the measurement step of frequency change caused by desorption S1-5, the heating and the vibration frequency measurement are performed repeatedly by the method similar to that of the sensitive film initialization and initial value acquisition step S1-1, and the measurement is finished at the point when the vibration frequency satisfies a predetermined determination condition, for example, a condition such that a change value or change rate of the frequency per unit time becomes a threshold value or less.

At the target molecule analysis step S1-6, pieces of data indicating the changes in the vibration frequency that are measured at the sensitive film initialization and initial value acquisition step S1-1, the measurement step of frequency change caused by adsorption S1-3, the measurement step of frequency change caused by desorption S1-5, and so on are processed in the signal processing unit 61, and from the processed data, at least one selected from the group consisting of the type and the concentration of the target molecules 11a is analyzed in the analyzer 62. In the case where a plurality of the detectors 30 are arranged in a matrix form, for example, it is possible to integrate and analyze pieces of information obtained from the respective detectors 30 and improve accuracies in estimating the type and the concentration of the target molecules 11a.

Figure 15:
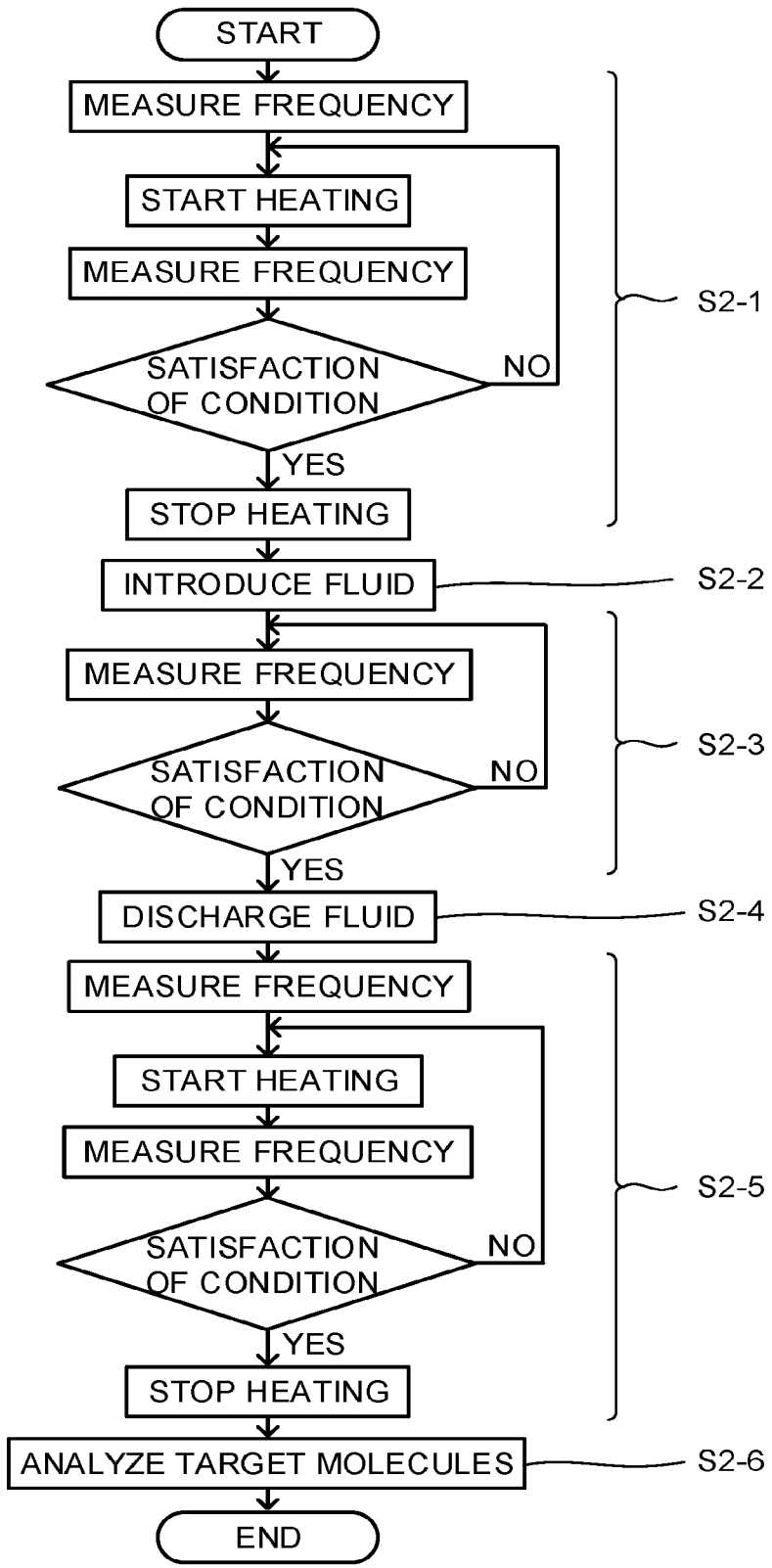
FIG. 15 is a flowchart for explaining another example of the detection method.

FIG. 15 is a flowchart for explaining another example of the detection method. This example of the detection method includes, as illustrated in FIG. 15, a sensitive film initialization and initial value acquisition step S2-1, a fluid introduction step S2-2, a measurement step of frequency change caused by adsorption S2-3, a fluid discharge step S2-4, a measurement step of frequency change caused by desorption S2-5, and a target molecule analysis step S2-6. This example is applicable to the case where the detector 30 has the structure illustrated in FIG. 6 and FIG. 7 or the structure illustrated in FIG. 8 to FIG. 10, for example, the driving electrodes for driving the vibrator 35 and the electrode having the function as a heater are independent, and the heating and the vibration frequency measurement are performed simultaneously.

At the sensitive film initialization and initial value acquisition step S2-1, first, the switching circuit 54 connects the detector 30 and the frequency measurement control circuit 51 and the first voltage is applied between the electrode 33 and the electrode 341 and the electrode 342, to thereby vibrate the vibrator 35 and start an initial vibration frequency measurement of the vibrator 35. Then, the switching circuit 54 connects the detector 30 and the heating control circuit 53 and the third voltage is applied to the electrodes 343 to 345, to thereby heat the sensitive film 37 and desorb the molecules attached to or adsorbed on the sensitive film 37. At this time, a temperature sensor (not illustrated) may be provided separately to control the temperature to a predetermined temperature. While heating the sensitive film 37 as above, the frequency is measured to acquire a difference between an initial value and a saturation value of the vibration frequency, for example, as data indicating the change in the vibration frequency. Incidentally, the ratio of a saturation value to an initial value of the vibration frequency may be acquired as the data indicating the change in the vibration frequency. The heating is stopped at the point when the frequency satisfies a predetermined determination condition, for example, a condition such that a change value or change rate of the frequency per unit time becomes a threshold value or less and the measurement is finished.

At the fluid introduction step S2-2, the fluid 1 is introduced into the detection unit 3 from the collection unit 2. The target molecules 11a contained in the fluid 1 are attached to or adsorbed on the sensitive film 37 in the detector 30.

At the measurement step of frequency change caused by adsorption S2-3, the switching circuit 54 connects the detector 30 and the frequency measurement control circuit 51 and the first voltage is applied between the electrode 33 and the electrode 341 and the electrode 342, to thereby vibrate the vibrator 35 and measure the vibration frequency of the vibrator 35. The vibration frequency of the vibrator 35 can be measured by using the electrode 36.

Figure 16:
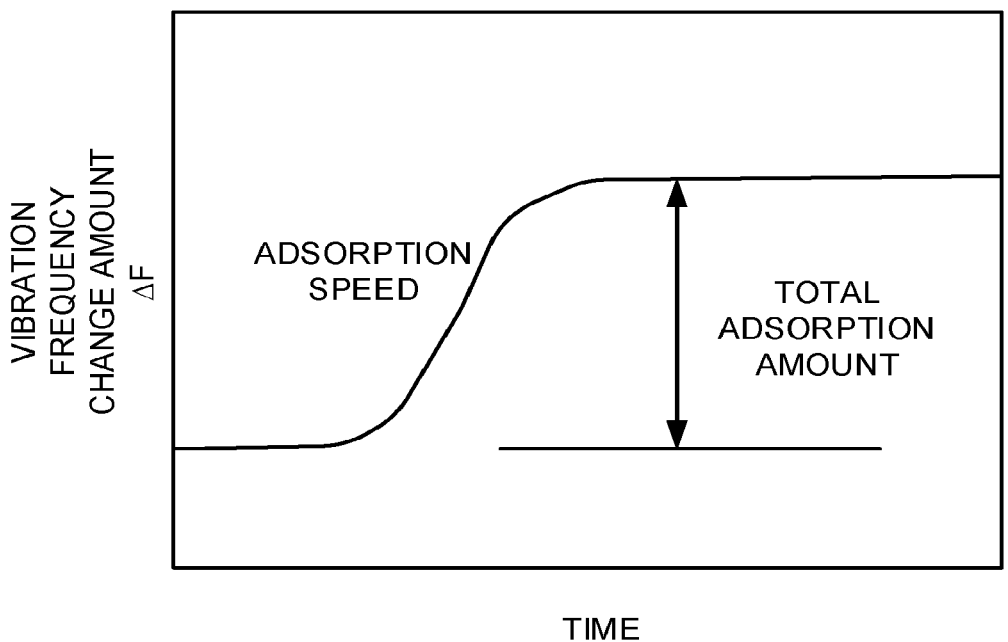
FIG. 16 is a view illustrating the relationship between a time and a change amount ΔF of a vibration frequency at the measurement step of frequency change caused by adsorption S2-3.

FIG. 16 is a view illustrating the relationship between a time and a change amount ΔF of the vibration frequency at the measurement step of frequency change caused by adsorption S2-3. The change amount ΔF of the vibration frequency increases because the molecules are attached or adsorbed with time, and thereafter is saturated. An inclination at this time corresponds to an adsorption speed of the molecules. Further, the difference between the initial value and the saturation value of the vibration frequency corresponds to the total adsorption amount of the molecules.

At the measurement step of frequency change caused by adsorption S2-3, the difference between an initial value and a saturation value of the vibration frequency, for example, is acquired as data indicating the change in the vibration frequency. Incidentally, the ratio of a saturation value to an initial value of the vibration frequency may be acquired as the data indicating the change in the vibration frequency. Measuring the frequency is continued until the frequency satisfies a predetermined determination condition, for example, a condition such that a change value or change rate of the frequency per unit time becomes a threshold value or less.

At the fluid discharge step S2-4, the fluid 1 is discharged through the discharge unit 4.

At the measurement step of frequency change caused by desorption S2-5, while heating the sensitive film 37 by the method similar to that of the sensitive film initialization and initial value acquisition step S2-1, the change in the vibration frequency is measured, and the measurement is finished at the point when the vibration frequency satisfies a predetermined determination condition, for example, a condition such that a change value or change rate of the frequency per unit time becomes a threshold value or less.

Figure 17:
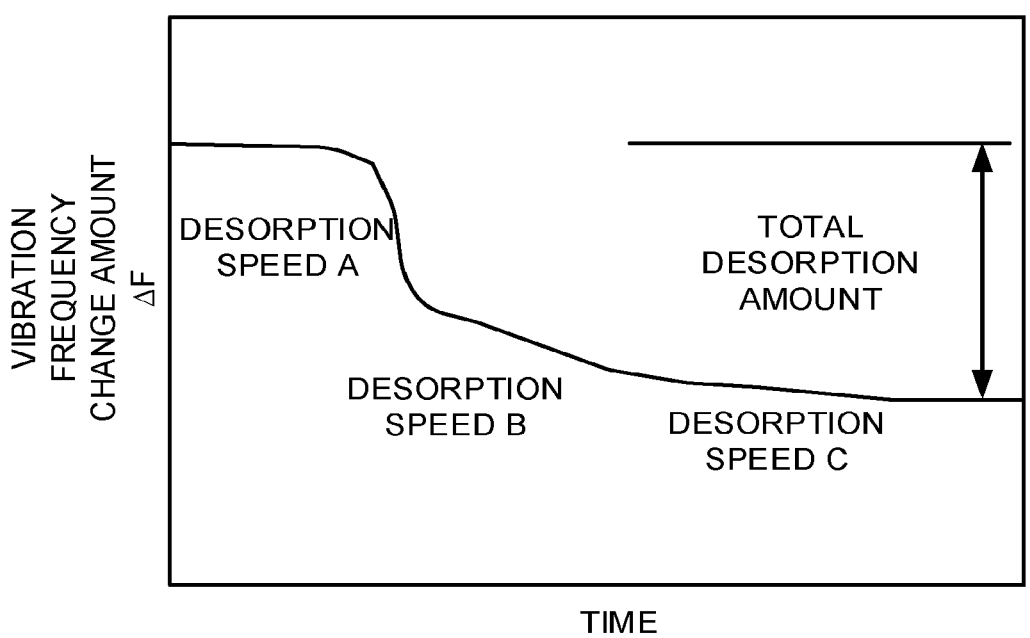
FIG. 17 is a view illustrating the relationship between a time and a change amount ΔF of the vibration frequency at the measurement step of frequency change caused by desorption S2-5.

FIG. 17 is a view illustrating the relationship between a time and a change amount ΔF of the vibration frequency at the measurement step of frequency change caused by desorption S2-5. The change amount ΔF of the vibration frequency decreases because the molecules are desorbed with time, and thereafter is saturated. An inclination at this time corresponds to a desorption speed of the molecules. FIG. 17 reveals that the molecules are desorbed at three-stage speeds of desorption speeds A, B, and C. This is because in the case of a plurality of molecules coexisting, differences are generated among the desorption speeds according to the strength of an interaction with the sensitive film 37. Acquiring data regarding such desorption speed differences is useful for improving accuracy in identifying molecular species. Further, the difference between the initial value and the saturation value of the vibration frequency corresponds to the total desorption amount of the molecules.

At the target molecule analysis step S2-6, pieces of data indicating the changes in the vibration frequency that are measured at the sensitive film initialization and initial value acquisition step S2-1, the measurement step of frequency change caused by adsorption S2-3, the measurement step of frequency change caused by desorption S2-5, and so on are processed in the signal processing unit 61, and from the processed data, at least one selected from the group consisting of the type and the concentration of the target molecules 11a is analyzed in the analyzer 62. In the case where a plurality of the detectors 30 are arranged in a matrix form, for example, it is possible to integrate and analyze pieces of information obtained from the respective detectors 30 and improve accuracies in estimating the type and the concentration of the target molecules 11a.

In this detection method example, while heating the sensitive film 37, the vibration frequency of the vibrator 35 is measured, thereby making it possible to detect the target molecules 11a by using the data indicating the change in the vibration frequency caused by desorption of the molecules from the sensitive film 37. This makes it possible to improve the detection accuracy of the target molecules 11a.

Figure 18:
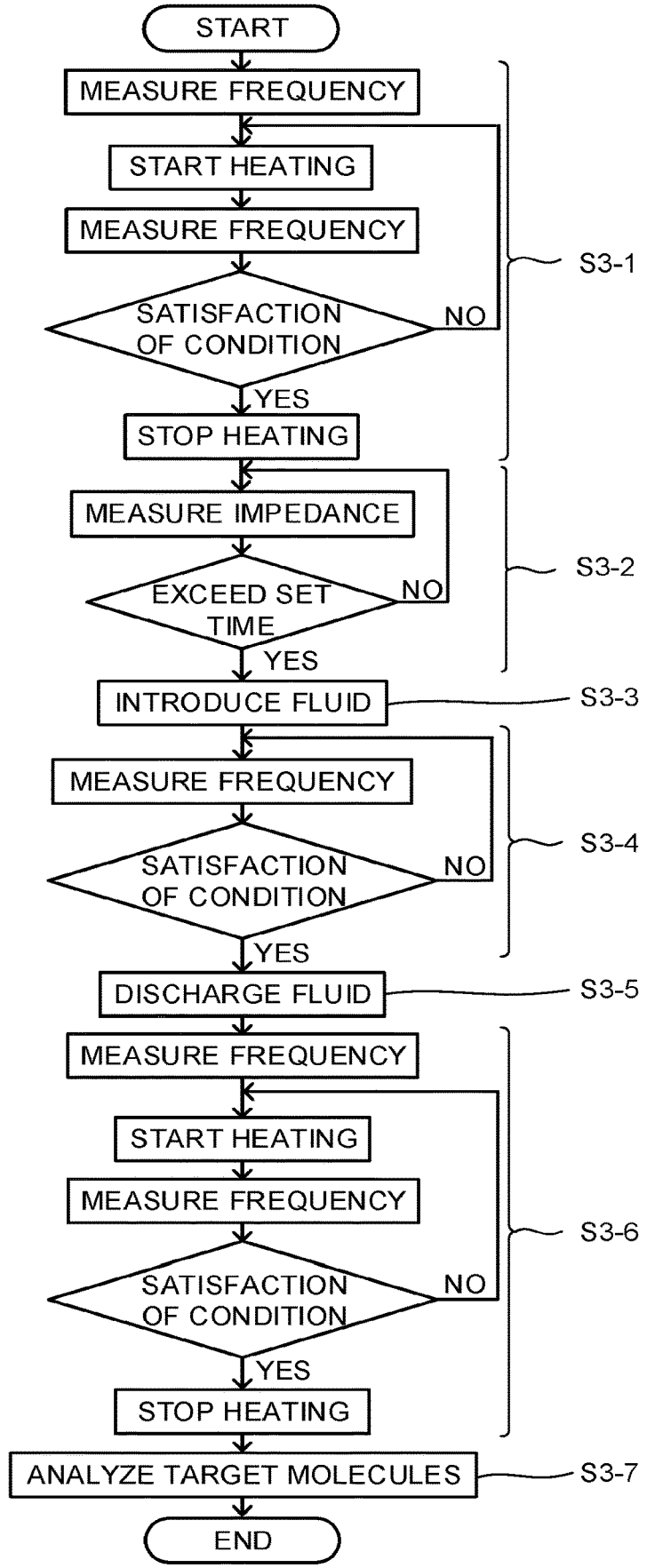
FIG. 18 is a flowchart for explaining another example of the detection method.

FIG. 18 is a flowchart for explaining another example of the detection method. This example of the detection method includes, as illustrated in FIG. 18, a sensitive film initialization and initial value acquisition step S3-1, a sensitive film impedance measurement step S3-2, a fluid introduction step S3-3, a measurement step of frequency change caused by adsorption S3-4, a fluid discharge step S3-5, and a measurement step of frequency change caused by desorption S3-6. This example is applicable to the case where the detector 30 has the structure illustrated in FIG. 8 to FIG. 10, for example.

At the sensitive film initialization and initial value acquisition step S3-1, similarly to the sensitive film initialization and initial value acquisition step S2-1, the switching circuit 54 first connects the detector 30 and the frequency measurement control circuit 51 and the first voltage is applied between the electrode 33 and the electrode 341 and the electrode 342, to thereby vibrate the vibrator 35 and start an initial vibration frequency measurement of the vibrator 35. Then, the switching circuit 54 connects the detector 30 and the heating control circuit 53 and the third voltage is applied to the electrodes 343 to 345, to thereby heat the sensitive film 37 and desorb the molecules attached to or adsorbed on the sensitive film 37. At this time, a temperature sensor (not illustrated) may be provided separately to control the temperature to a predetermined temperature. While heating the sensitive film 37 as above, the frequency is measured to acquire a difference between an initial value and a saturation value of the vibration frequency, for example, as data indicating the change in the vibration frequency. Incidentally, the ratio of a saturation value to an initial value of the vibration frequency may be acquired as the data indicating the change in the vibration frequency. The heating is stopped at the point when the frequency satisfies a predetermined determination condition, for example, a condition such that a change value or change rate of the frequency per unit time becomes a threshold value or less and the measurement is finished.

At the sensitive film impedance measurement step S3-2, the switching circuit 54 connects the detector 30 and the impedance measurement control circuit 52 and the second voltage is applied between the electrode 344 and the electrode 345, to thereby measure the impedance of the sensitive film 37. At the impedance measurement step S2-2, the measurement is finished after a lapse of a predetermined time period. The measurement of the impedance is continued in the case where a predetermined time period does not elapse.

The change in the impedance of the sensitive film 37 is thought to be greatly affected by a relative permittivity of the adsorbed molecules. Water has a relative permittivity as extremely high as 80 and its molecules are detected most easily, and in addition to this, for example, ethanol has a relative permittivity of 24, and further molecules having a polar group (or a functional group) such as a hydroxyl group, a carboxyl group, a carbonyl group, or an amino group has a large relative permittivity. In contrast to this, molecules of hydrocarbon series tend to be low in relative permittivity as represented by 1.9 of hexane. However, the change in capacity caused by adsorption of the molecules of course relies on an adsorbed amount of the molecules, and thus combining with information on the adsorbed amount change caused by the change in the vibration frequency makes it possible to improve the detection accuracy and the detection sensitivity of the target molecules.

As problems of the detector having the sensitive film 37, for example, the decrease in detection sensitivity of the target molecules 11a caused by adsorption of moisture on the sensitive film 37 and erroneous detection are cited. In contrast to this, it is thought that, for example, electrodes are formed on and under the sensitive film formed on the detector to measure the impedance, to thereby estimate humidity and correct data obtained from the detector.

However, the above-described structure may inhibit attachment or adsorption of the target molecules because the top surface of the sensitive film is covered with the electrode. On the other hand, the structure of the detector 30 does not inhibit attachment or adsorption of the target molecules 11a because the sensitive film 37 is formed on the electrodes 341, 342 and it is not necessary to form electrodes on the top surface of the sensitive film 37.

At the fluid introduction step S3-3, the fluid 1 is introduced into the detection unit 3 from the collection unit 2. The target molecules 11a contained in the fluid 1 are attached to or adsorbed on the sensitive film 37 in the detector 30.

At the measurement step of frequency change caused by adsorption S3-4, the switching circuit 54 connects the detector 30 and the frequency measurement control circuit 51 and the first voltage is applied between the electrode 33 and the electrode 341 and the electrode 342, to thereby vibrate the vibrator 35 and measure the vibration frequency of the vibrator 35. The vibration frequency of the vibrator 35 can be measured by using the electrode 36.

At the measurement step of frequency change caused by adsorption S3-4, the difference between an initial value and a saturation value of the vibration frequency, for example, is acquired as data indicating the change in the vibration frequency. Incidentally, the ratio of a saturation value to an initial value of the vibration frequency may be acquired as the data indicating the change in the vibration frequency. Measuring the frequency is continued until the frequency satisfies a predetermined determination condition, for example, a condition such that a change value or change rate of the frequency per unit time becomes a threshold value or less.

At the fluid discharge step S3-5, the fluid 1 is discharged through the discharge unit 4.

At the measurement step of frequency change caused by desorption S3-6, while heating the sensitive film 37 by applying the third voltage between the electrode 344 and the electrode 345 by the method similar to that of the sensitive film initialization and initial value acquisition step S3-1, the change in the vibration frequency is measured, and the measurement is finished at the point when the vibration frequency satisfies a predetermined determination condition, for example, a condition such that a change value or change rate of the frequency per unit time becomes a threshold value or less.

At the target molecule analysis step S3-7, data indicating the impedance measured at the sensitive film impedance measurement step S3-2 and pieces of data indicating the changes in the vibration frequency that are measured at the measurement step of frequency change caused by adsorption S3-4 and the measurement step of frequency change caused by desorption S3-6 are processed in the signal processing unit 61, and from the processed data, at least one selected from the group consisting of the type and the concentration of the target molecules 11a is analyzed in the analyzer 62.

In this detection method example, before the fluid 1 is introduced, the impedance of the sensitive film 37 is measured, thereby making it possible to detect the target molecules 11a by using the data indicating the change in the impedance caused by attachment of moisture or the like to the sensitive film 37. In the case of a measurement environment being the atmosphere, for example, the humidity can be measured. This makes it possible to improve the detection sensitivity and the detection accuracy of the target molecules 11a.

Figure 19:
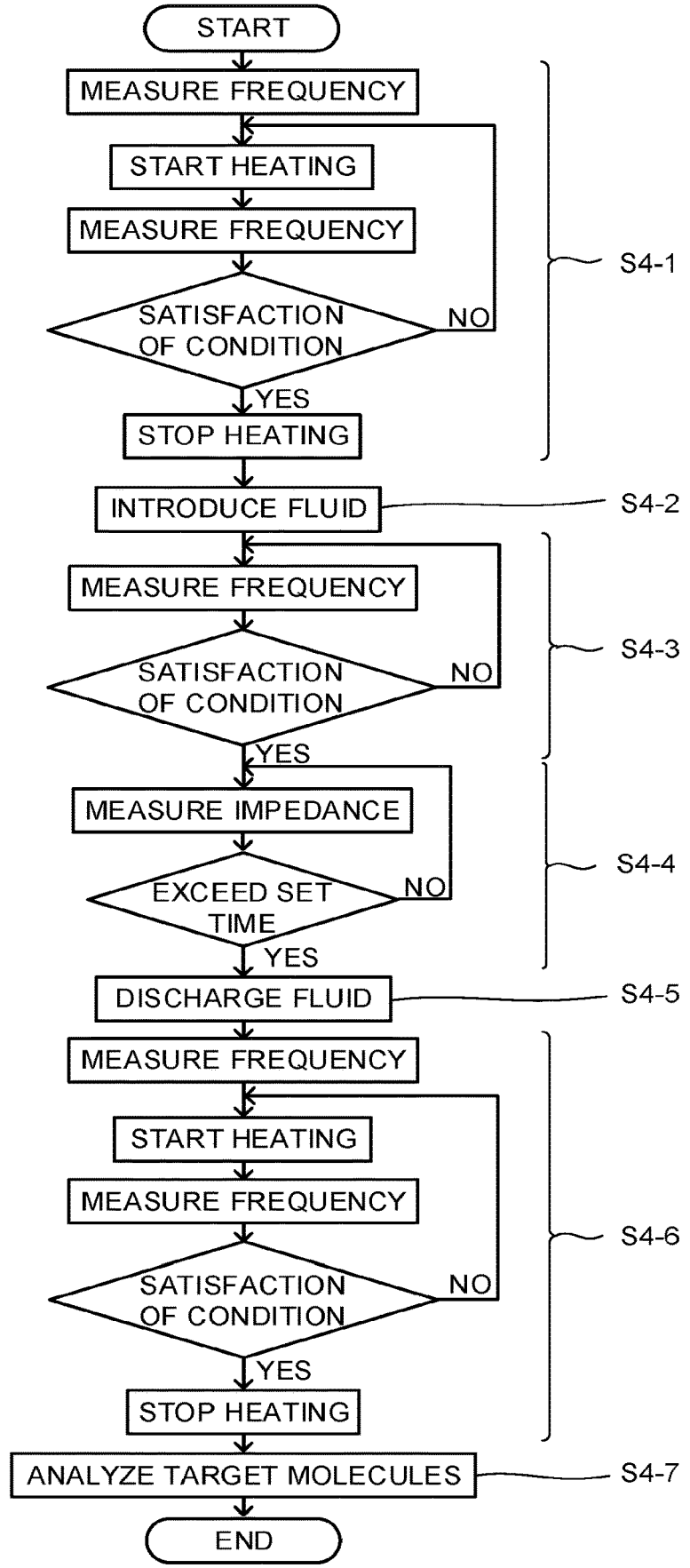
FIG. 19 is a flowchart for explaining another example of the detection method.

FIG. 19 is a flowchart for explaining another example of the detection method. This example of the detection method includes, as illustrated in FIG. 19, a sensitive film initialization and initial value acquisition step S4-1, a fluid introduction step S4-2, a measurement step of frequency change caused by adsorption S4-3, a sensitive film impedance measurement step S4-4, a fluid discharge step S4-5, a measurement step of frequency change caused by desorption S4-6, and a target molecule analysis step S4-7. This example is applicable to the case where the detector 30 has the structure illustrated in FIG. 8 to FIG. 10, for example.

At the sensitive film initialization and initial value acquisition step S4-1, similarly to the sensitive film initialization and initial value acquisition step S3-1, the switching circuit 54 first connects the detector 30 and the frequency measurement control circuit 51 and the first voltage is applied between the electrode 33 and the electrode 341 and the electrode 342, to thereby vibrate the vibrator 35 and start an initial vibration frequency measurement of the vibrator 35. Then, the switching circuit 54 connects the detector 30 and the heating control circuit 53 and the third voltage is applied to the electrodes 343 to 345, to thereby heat the sensitive film 37 and desorb the molecules attached to or adsorbed on the sensitive film 37. At this time, a temperature sensor (not illustrated) may be provided separately to control the temperature to a predetermined temperature. While heating the sensitive film 37 as above, the frequency is measured to acquire a difference between an initial value and a saturation value of the vibration frequency, for example, as data indicating the change in the vibration frequency. Incidentally, the ratio of a saturation value to an initial value of the vibration frequency may be acquired as the data indicating the change in the vibration frequency. The heating is stopped at the point when the frequency satisfies a predetermined determination condition, for example, a condition such that a change value or change rate of the frequency per unit time becomes a threshold value or less, and the measurement is finished.

At the fluid introduction step S4-2, the fluid 1 is introduced into the detection unit 3 from the collection unit 2. The target molecules 11a contained in the fluid 1 are attached to or adsorbed on the sensitive film 37 in the detector 30.

At the measurement step of frequency change caused by adsorption S4-3, the switching circuit 54 connects the detector 30 and the frequency measurement control circuit 51 and the first voltage is applied between the electrode 33 and the electrode 341 and the electrode 342, to thereby vibrate the vibrator 35 and measure the vibration frequency of the vibrator 35. The vibration frequency of the vibrator 35 can be measured by using the electrode 36.

At the measurement step of frequency change caused by adsorption S4-3, the difference between an initial value and a saturation value of the vibration frequency, for example, is acquired as data indicating the change in the vibration frequency. Incidentally, the ratio of a saturation value to an initial value of the vibration frequency may be acquired as the data indicating the change in the vibration frequency. Measuring the frequency is continued until the frequency satisfies a predetermined determination condition, for example, a condition such that a change value or change rate of the frequency per unit time becomes a threshold value or less.

At the sensitive film impedance measurement step S4-4, the switching circuit 54 connects the detector 30 and the impedance measurement control circuit 52 and the second voltage is applied between the electrode 344 and the electrode 345, to thereby measure the impedance of the sensitive film 37. At the impedance measurement step S4-4, the measurement is finished after a lapse of a predetermined time period. The measurement of the impedance is continued in the case where a predetermined time period does not elapse.

At the fluid discharge step S4-5, the fluid 1 is discharged through the discharge unit 4.

At the measurement step of frequency change caused by desorption S4-6, while heating the sensitive film 37 by applying the third voltage between the electrode 344 and the electrode 345 by the method similar to that of the sensitive film initialization and initial value acquisition step S4-1, the change in the vibration frequency is measured, and the measurement is finished at the point when the vibration frequency satisfies a predetermined determination condition, for example, a condition such that a change value or change rate of the frequency per unit time becomes a threshold value or less.

At the target molecule analysis step S4-7, data indicating the impedance measured at the sensitive film impedance measurement step S4-4 and pieces of data indicating the changes in the vibration frequency that are measured at the measurement step of frequency change caused by adsorption S4-3 and the measurement step of frequency change caused by desorption S4-6 are processed in the signal processing unit 61, and from the processed data, at least one selected from the group consisting of the type and the concentration of the target molecules 11a is analyzed in the analyzer 62.

In this detection method example, after the fluid 1 is introduced, the impedance of the sensitive film 37 is measured, thereby making it possible to detect the target molecules 11a by using the data indicating the change in the impedance caused by the target molecules 11a. This makes it possible to improve the detection accuracy of the target molecules 11a.

EXAMPLE

Example 1

A molecular detection apparatus including the detector 30 having the structure illustrated in FIG. 6 was fabricated. The electrodes 341, 342 are gold electrodes. The sensitive film 37 having HKUST-1 was formed in an about 100-μm-square area on the surface 32b. A HKUST-1 powder (Basolite (registered trademark) C 300) produced by Sigma-Aldrich Co. LLC was used to prepare a 10 mg/ml pure water dispersion liquid. Several drops of the above-described dispersion liquid were applied onto the previously-described area by using an industrial ink jet device to be dried for three hours in an oven at 60° C.

A mixed gas adjusted to 10 ppm by diluting an ethylene gas with a nitrogen gas was enclosed within a sampling bag, and a sample gas was formed. This sampling bag was connected to the molecular detection apparatus to suck the sample gas by a pump and introduce the sample gas into the detection unit 3. Thereafter, the target molecules 11a were detected in accordance with the flowchart illustrated in FIG. 15.

Due to 10 ppm of ethylene gas, the change amount of the vibration frequency of the vibrator 35 was 50 Hz. Since the change amount of the vibration frequency per unit time after heating of the sensitive film 37 and discharge of the sample gas was a threshold value or less, it was determined that the molecules adsorbed on the sensitive film 37 were desorbed, and the measurement was finished. This example made it possible to detect 10 ppm of ethylene gas in the sample gas.

Example 2

A detection apparatus including the detector 30 having the structure illustrated in FIG. 8 and FIG. 9 was fabricated. The electrode 341 to the electrode 345 are gold electrodes. The sensitive film 37 having HKUST-1 was formed in an about 100-μm-square area on the surface 32b.

A mixed gas adjusted to 10 ppm by diluting an acetylene gas with the atmosphere was enclosed within a sampling bag, and a sample gas was formed. This sampling bag was connected to the detection apparatus to suck the sample gas by a pump and introduce the sample gas into the detection unit 3. Thereafter, the target molecules 11a were detected in accordance with the flowchart illustrated in FIG. 18.

As a result that the impedance was measured before introduction of the fluid 1, it was found out that relative humidity in a measurement environment (20° C.) is about 40% RH. Then, the fluid 1 was introduced and data indicating the change in the vibration frequency of the vibrator 35 caused by adsorption of ethylene gas were acquired. The relationship between the change amount of the vibration frequency of the vibrator 35 and the concentration of ethylene in the atmosphere varies according to the humidity of the atmosphere, and thus a table for correction was acquired beforehand and the concentration of ethylene was estimated from a relational expression using data indicating the relative humidity of 40% RH, which were obtained by measuring the impedance. Since the change amount of the vibration frequency per unit time after heating of the sensitive film 37 and discharge of the sample gas was a threshold value or less, it was determined that the molecules adsorbed on the sensitive film 37 were desorbed, and the measurement was finished. This example made it possible to detect 10 ppm of acetylene gas in the sample gas.

Example 3

A detection apparatus including the detector 30 having the structure illustrated in FIG. 11 to FIG. 13 was used. The electrodes 341, 342 are gold electrodes. The sensitive film 37 having HKUST-1 was formed in an about 100-μm-square area on the surface 32b.

A mixed gas adjusted to 10 ppm by diluting an ethylene gas with a nitrogen gas was enclosed within a sampling bag, and a sample gas was formed. This sampling bag was connected to the detection apparatus to suck the sample gas by a pump and introduce the sample gas into the detection unit 3. Thereafter, the target molecules 11a were detected in accordance with the flowchart illustrated in FIG. 19.

The fluid 1 was introduced and data indicating the change in the vibration frequency of the vibrator 35 caused by adsorption of ethylene gas were acquired. Then, the impedance was measured and it was confirmed that polar molecules (water, carbon monoxide, and so on) other than ethylene were not adsorbed. Since the change amount of the vibration frequency per unit time after heating of the sensitive film 37 and discharge of the sample gas was a threshold value or less, it was determined that the molecules adsorbed on the sensitive film 37 were desorbed, and the measurement was finished. This example made it possible to detect 10 ppm of ethylene gas in the sample gas.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A molecular detection apparatus comprising a detector, the detector including:
   a vibrator having
      a piezoelectric member that has a first surface and a second surface,
      a first electrode that is connected to the first surface,
      a second electrode that is connected to the second surface, and
      a third electrode that is connected to the second surface and is disconnected from the second electrode;
   a sensitive film overlapping at least one part of the second electrode and at least one part of the third electrode and configured to change a vibration frequency of the vibrator in response to an interaction with target molecules; and
   a detection electrode to detect the changed vibration frequency, wherein,
   each of the second and third electrodes has a function as a driving electrode to drive the piezoelectric member and vibrate the vibrator.

2. A molecular detection apparatus comprising a detector, the detector including:
   a vibrator having
      a piezoelectric member that has a first surface and a second surface,
      a first electrode that is provided on the first surface,
      a second electrode that is provided on the second surface, and
      a third electrode that is provided on the second surface and is spaced from the second electrode;
   a sensitive film overlapping at least one part of the second electrode and at least one part of the third electrode and configured to change a vibration frequency of the vibrator in response to an interaction with target molecules; and
   a detection electrode provided on the second surface, spaced from the second and the third electrodes, and configured to detect the changed vibration frequency, wherein,
   each of the second and third electrodes has a function as a driving electrode to drive the piezoelectric member and vibrate the vibrator.

3. The apparatus according to claim 1, wherein each of the second and the third electrodes has a function as a functional electrode to measure an impedance of the sensitive film.

4. The apparatus according to claim 1, wherein the second and the third electrodes have at least one shape selected from the group consisting of comb-teeth shapes facing each other and shapes continuously bending on the first surface.

5. The apparatus according to claim 1, wherein the detector further includes a fourth electrode provided on the second surface and spaced from the second and the third electrodes, and the fourth electrode has a shape continuously bending between the second surface and the sensitive film.

6. The apparatus according to claim 1, wherein the detector further includes:
   a fourth electrode provided on the second surface and spaced from the second and the third electrodes; and
   a fifth electrode provided on the second surface and spaced from the second to fourth electrodes, and the fourth and the fifth electrodes have at least one shape selected from the group consisting of comb-teeth shapes facing each other and shapes continuously bending, the at least one shape being provided between the second surface and the sensitive film.

7. The apparatus according to claim 6, wherein each of the fourth and the fifth electrodes have a function as a functional electrode to measure an impedance of the sensitive film.

8. The apparatus according to claim 4, wherein the third electrode has a function as a heater to heat the sensitive film to desorb molecules attached to or absorbed on the sensitive film.

9. The apparatus according to claim 1, wherein the sensitive film has a metal organic framework.

10. The apparatus according to claim 9, wherein the metal organic framework contains a coordinatively unsaturated metal site.

11. The apparatus according to claim 10, wherein the metal organic framework has HKUST-1.

12. The apparatus according to claim 1, further comprising:
a control unit including:
a frequency measurement control circuit to control measurement of the vibration frequency of the vibrator;
an impedance measurement control circuit to control measurement of the impedance of the sensitive film;
a heating control circuit to control heating of the sensitive film; and
a switching circuit to switch connection between the detector and the impedance measurement control circuit, connection between the detector and the frequency measurement control circuit, and connection between the detector and the heating control circuit.

13. The apparatus according to claim 12, further comprising:
an analysis unit to detect at least one selected from the group consisting of a type and a concentration of the target molecules in accordance with at least one data selected from the group consisting of data indicating a change in the vibration frequency in response to attachment or adsorption of molecules to or on the sensitive film, data indicating the impedance, and data indicating a change in the vibration frequency in response to desorption of the molecules from the sensitive film.

14. The apparatus according to claim 13, further comprising:
a plurality of the detectors, wherein
the analysis unit is configured to detect at least one selected from the group consisting of a type and a concentration of the target molecules in accordance with at least one data selected from the group consisting of, in each of the detectors, data indicating a change in the vibration frequency in response to attachment or adsorption of molecules to or on the sensitive film, data indicating the impedance, and data indicating a change in the vibration frequency in response to desorption of the molecules from the sensitive film.

15. The apparatus according to claim 1, wherein the first electrode is electrically connected to the first surface,
the second electrode is electrically connected to the second surface, and
the third electrode is electrically connected to the second surface and is electrically disconnected from the second electrode.

* * * * *